(12) United States Patent
Lee et al.

(10) Patent No.: US 11,131,231 B2
(45) Date of Patent: Sep. 28, 2021

(54) OXYGEN SENSOR FOR VEHICLE

(71) Applicant: HYUNDAI KEFICO CORPORATION, Gunpo-si (KR)

(72) Inventors: Dae-Gun Lee, Anyang-si (KR); Yang-Joo Ko, Seongnam-si (KR); Kyeong-Hyeon Kim, Anyang-si (KR); Jung-Taek Kim, Bucheon-si (KR); Ki-Won Sung, Seoul (KR); Seung-Tae Lee, Seoul (KR)

(73) Assignee: HYUNDAI KEFICO CORPORATION, Gyeonggi-do (KR)

( * ) Notice: Subject to any disclaimer, the term of this patent is extended or adjusted under 35 U.S.C. 154(b) by 252 days.

(21) Appl. No.: 16/532,847

(22) Filed: Aug. 6, 2019

(65) Prior Publication Data

US 2020/0049054 A1    Feb. 13, 2020

(30) Foreign Application Priority Data

Aug. 7, 2018   (KR) .......................... 10-2018-0091745

(51) Int. Cl.
*F01N 11/00*  (2006.01)
*G01N 33/00*  (2006.01)

(52) U.S. Cl.
CPC ....... *F01N 11/007* (2013.01); *G01N 33/0009* (2013.01); *F01N 2560/025* (2013.01)

(58) Field of Classification Search
CPC .. F01N 11/007; F01N 13/008; F01N 13/1844; F01N 2260/18; F01N 2450/18; F01N 2560/025; F01N 2570/16; F01N 3/2839; F01N 2610/148; G01N 33/0009; G01N 27/4077; G01N 27/4078
See application file for complete search history.

(56) References Cited

U.S. PATENT DOCUMENTS

| 2012/0006093 | A1* | 1/2012 | Yamada | ............. | G01N 27/4078 73/23.31 |
| 2016/0087289 | A1* | 3/2016 | Shim | ................. | H01M 8/04231 429/414 |

FOREIGN PATENT DOCUMENTS

| JP | 2007-315952 A | † | 12/2007 |
| JP | 2012-18016 A | † | 1/2012 |
| KR | 100579246 B1 | | 5/2006 |

* cited by examiner
† cited by third party

*Primary Examiner* — John Fitzgerald
*Assistant Examiner* — Truong D Phan
(74) *Attorney, Agent, or Firm* — Mintz Levin Cohn Ferris Glovsky and Popeo, P.C.; Peter F. Corless

(57) ABSTRACT

The proposed technology relates to an oxygen sensor for a vehicle, the oxygen sensor including a housing, a sleeve coupled to the housing, a sensor element configured to determine an oxygen concentration and provided within an inner space defined by the housing and the sleeve, a contact terminal connected to the sensor element, a contact bush including an upper bush and a lower bush, and a positioning unit coupled with the contact bush and maintaining a gap between a circumference of the contact bush and an inner side surface of the sleeve. In particular, the contact bush is coupled with the sensor element and the terminal at the center of the sleeve, and movement due to external impact is prevented.

10 Claims, 7 Drawing Sheets

OXYGEN SENSOR FOR VEHICLE

CROSS REFERENCE TO RELATED APPLICATION(S)

This application claims the benefit of Korean Patent Application No. 10-2018-0091745, filed on Aug. 7, 2018, which application is hereby incorporated by reference in its entirety.

BACKGROUND

1. Technical Field

The present disclosure relates to an oxygen sensor for a vehicle.

2. Description of the Related Art

In general, an oxygen sensor is used in a vehicle to detect oxygen concentration in exhaust gas of the vehicle, and enables to control air-fuel ratio and thus to reduce emission of noxious gas. In the oxygen sensor, a sensor element determining an oxygen concentration in exhaust gas of the vehicle is provided in a housing and a sleeve, and determines an oxygen concentration in the exhaust gas. Subsequently, a signal detected by the sensor element is transmitted to a controller through a terminal.

In particular, the terminal is mounted to a bush or the like in the housing, and the bush is coupled in the housing in an elastically supported state by a spring or the like to prevent the sensor element from moving due to external vibration or impact. However, there may be a problem that the bush is assembled without being centered in the sleeve, and thus other parts within the sleeve also become poor in alignment, which may cause problems in detecting precise oxygen concentration and in signal transmission of the detecting result.

The foregoing is intended merely to aid in the understanding of the background of the present disclosure, and is not intended to mean that the present disclosure falls within the purview of the related art that is already known to those skilled in the art.

SUMMARY

The present disclosure has been made in an effort to solve the problems, and an object of the present disclosure is to provide an oxygen sensor for a vehicle, wherein a contact bush that is coupled with a sensor element and a terminal is coupled at the center of a sleeve, and movement thereof due to external impact is prevented.

In order to achieve the objects of the present disclosure, an oxygen sensor for a vehicle according to an exemplary embodiment of the present disclosure may include a housing; a sleeve coupled to a side of the housing; a sensor element configured to determine an oxygen concentration and provided within an inner space defined by the housing and the sleeve; a contact terminal connected to the sensor element; a contact bush including an upper bush and a lower bush, the upper bush being open upwardly to form a sensor groove into which the sensor element is inserted and the lower bush being open downwardly to form a terminal groove into which the contact terminal is inserted; and a positioning unit coupled with the contact bush. The positioning unit may maintain a gap between a circumference of the contact bush and an inner side surface of the sleeve.

Further, the upper bush may include at least two positioning grooves at a side surface thereof, the positioning unit may include at least two bush side surface supports inserted into the at least two positioning grooves, and each of the bush side surface supports may include a bush side surface support end that is bent outward to allow the bush side surface support end to be in contact with the inner side surface of the sleeve. The bush side surface support may be divided into three parts in a width direction of the positioning groove, and the bush side surface support end that is bent outward may correspond to an upper end of a middle part among the three parts of the bush side surface support.

The oxygen sensor may further include a disc spring formed in a plate shape with a central aperture, the disc spring being inclined downwardly in a sectional view. In particular, an outer circumference of the disc spring may be disposed on the sleeve, and an inner circumference of the disc spring may support the contact bush. Further, the positioning unit may include a bush lower surface support that supports a lower surface of the contact bush, the bush lower surface support including at least two spring support protrusions which protrude downwardly with an inclination to support a lower surface of the disc spring.

The lower bush of the contact bush may have a smaller diameter than the upper bush to allow a step to be formed between the lower bush and the upper bush, and the inner circumference of the disc spring may support the step between the upper bush and the lower bush.

The sleeve may include a step at a center part thereof to allow a diameter of a lower part of the sleeve to be smaller than a diameter of an upper part thereof with respect to the step, and the outer circumference of the disc spring may be disposed on the step of the sleeve. Alternatively, the outer circumference of the disc spring may be fitted into a spring seat groove provided on the step of the sleeve by pressure.

Meanwhile, the positioning unit may include the bush lower surface support that supports the lower surface of the contact bush; and the bush side surface support that supports the side surface of the contact bush. In particular, the upper bush may include at least two positioning grooves partially formed on an upper portion of the side surface of the upper bush, and the bush side surface support may include a support end at a position that corresponds to each of the at least two positioning grooves, the support end may be bent from an upper end thereof and be inserted into the positioning groove. The bush side surface support may include the bush side surface support end that protrudes outward, and the bush side surface support end may be in contact with the inner side surface of the sleeve. The bush side surface support end may include a first curved portion and a second curved portion, the first curved portion being bent outward from a lower portion thereof and the second curved portion being bent inward from the first curved portion.

The oxygen sensor may further include a disc spring formed in a plate shape with a central aperture, the disc spring being inclined downwardly in a sectional view. An outer circumference of the disc spring may be disposed on the sleeve, and an inner circumference of the disc spring may supports the contact bush. The bush lower surface support may include at least two spring support protrusions which extend downwardly from an inside of the bush lower surface support and then are curved outwardly from the bush lower surface support.

According to the oxygen sensor for the vehicle of the present disclosure, the positioning unit may be coupled with the contact bush and the disc spring together, and the contact bush may be aligned in the desired position when assembling the contact bush. In addition, when the contact bush is coupled in the sleeve, the contact bush may maintain a predetermined distance from the inner side surface of the sleeve by the positioning unit to allow the position of the contact bush to be secured at the center of the sleeve, and therefore, the contact bush may be prevented from moving due to external impact or the like.

BRIEF DESCRIPTION OF THE DRAWINGS

The above and other objects, features and advantages of the present disclosure will be more clearly understood from the following detailed description taken in conjunction with the accompanying drawings, in which.

DETAILED DESCRIPTION

Hereinafter, in order to understand the present disclosure, operational advantages of the present disclosure, and objectives achieved by embodying the present disclosure, reference will be made in detail to various exemplary embodiments of the present disclosure, exemplary examples of which are illustrated in the accompanying drawings and described below.

In the following description, when the detailed description of the known art related to the present disclosure may obscure the gist of the present disclosure, the detailed description thereof will be omitted.

It is understood that the term "vehicle" or "vehicular" or other similar term as used herein is inclusive of motor vehicles in general such as passenger automobiles including sports utility vehicles (SUV), buses, trucks, various commercial vehicles, watercraft including a variety of boats and ships, aircraft, and the like, and includes hybrid vehicles, electric vehicles, combustion, plug-in hybrid electric vehicles, hydrogen-powered vehicles and other alternative fuel vehicles (e.g. fuels derived from resources other than petroleum).

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items.

Unless specifically stated or obvious from context, as used herein, the term "about" is understood as within a range of normal tolerance in the art, for example within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

Figure 1:
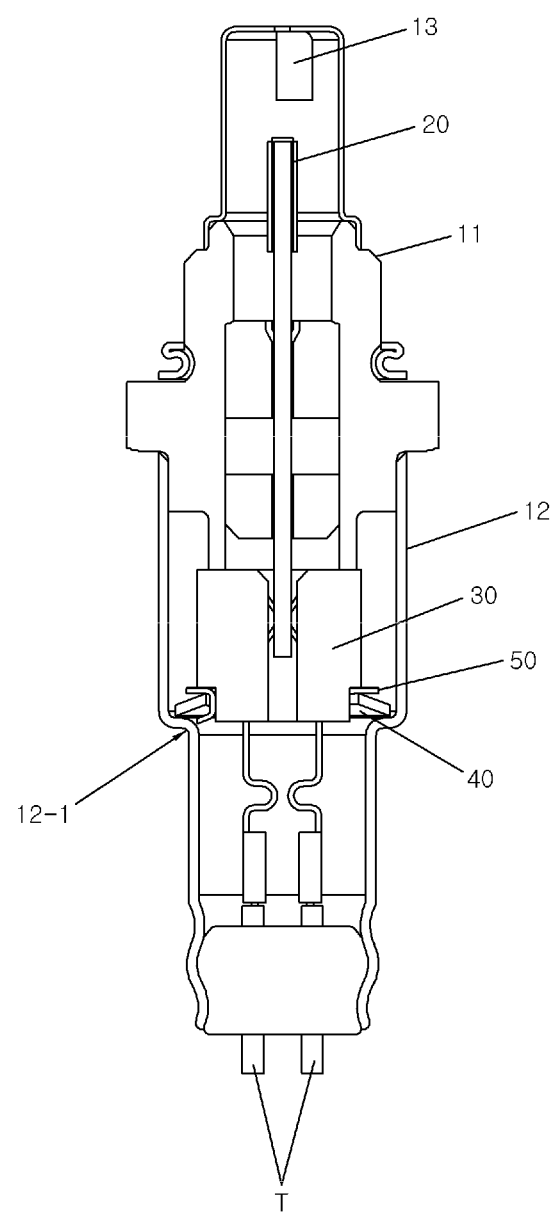
FIG. 1 is a sectional view showing an oxygen sensor for a vehicle according to a first exemplary embodiment of the present disclosure.
Figure 2A:
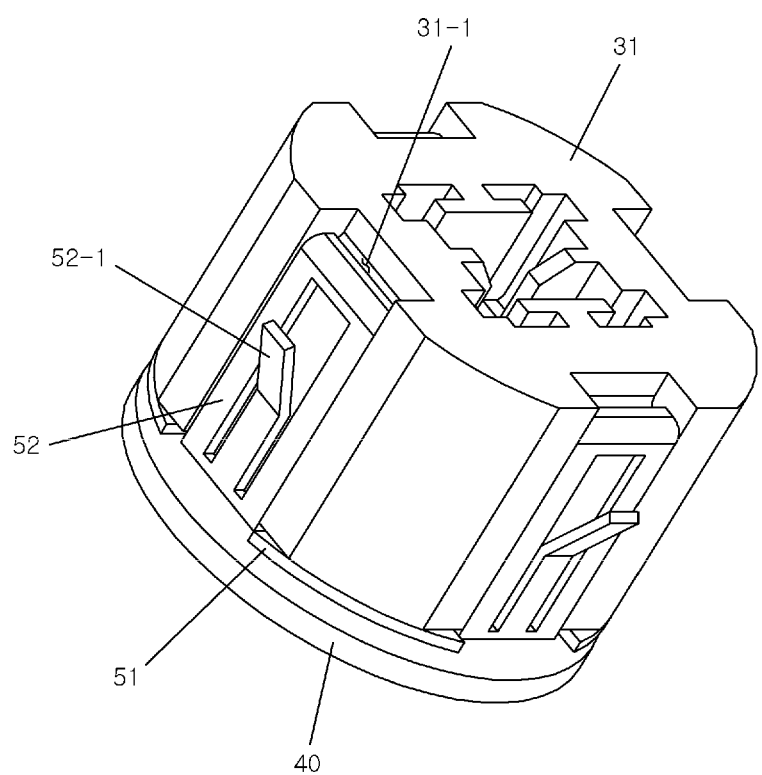
FIGS. 2A and 2B are views showing a coupling state of a contact bush, a disc spring, and a positioning unit of the oxygen sensor for the vehicle according to the first exemplary embodiment of the present disclosure.
Figure 2B:
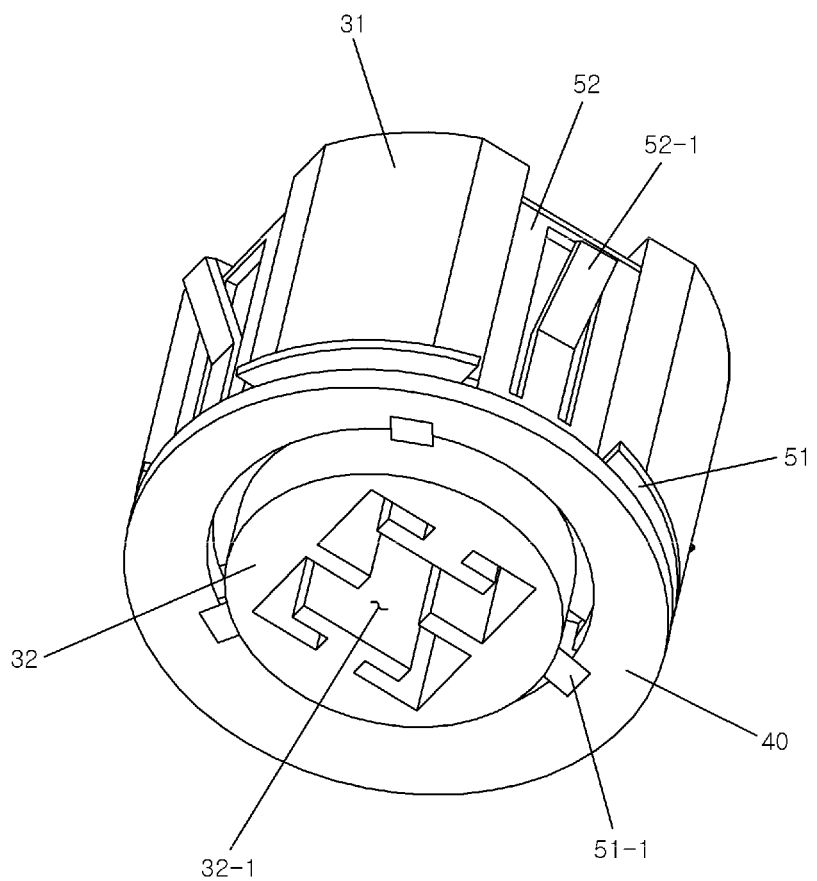

FIG. 1 is a sectional view showing an oxygen sensor for a vehicle according to a first exemplary embodiment of the present disclosure. FIGS. 2A and 2B are views showing a coupling state of a contact bush, a disc spring, and a positioning unit of the oxygen sensor for the vehicle according to the first exemplary embodiment of the present disclosure.

Hereinafter, the oxygen sensor for the vehicle according to the first exemplary embodiment of the present disclosure will be described with reference to FIGS. 1 to 2B.

The oxygen sensor according to the present disclosure is for measuring oxygen concentration of exhaust gas of a vehicle, the oxygen sensor may be formed by coupling a housing 11 having an inner space and a sleeve 12 for coupling with another device, as shown in FIG. 1. Thus, a sensor element 20 configured to determine an oxygen concentration may be provided within the inner space formed by the housing 11 and the sleeve 12, and a protective tube 13 may be coupled to the housing 11 to protect the sensor element 20 exposed to the upper portion of the housing.

The sensor element 20, the contact bush 30, the disc spring 40, and the positioning unit 50 may be provided in the sleeve 12. For elastic-support coupling of the contact bush 30, the sleeve 12 may include a step 12-1 at a middle portion thereof, to allow a lower portion of the sleeve to have a diameter smaller than a diameter of an upper portion thereof with respect to the step 12-1.

The contact bush 30 may be coupled in the sleeve while being elastically supported by the disc spring 40 disposed on the step 12-1. As shown in FIGS. 2A and 2B, the disc spring 40 may be formed in a plate shape with a central aperture, and may also have a shape of being inclined downwardly from an inner circumference toward an outer circumference when viewed in a sectional view. Therefore, the outer circumference of the disc spring 40 may be disposed on the step 12-1, and the inner circumference thereof may support a step of the contact bush 30.

The contact bush 30 may include an upper bush 31 and a lower bush 32, the upper bush 31 being open upwardly to form a sensor groove into which the sensor element 20 is inserted and the lower bush 32 being open downwardly to form a terminal groove 32-1 into which a contact terminal T is inserted. The lower bush 32 may have a smaller diameter than a diameter of the upper bush 31, and accordingly, a step may be formed between the upper bush 31 and the lower bush 32.

The contact terminal T may be configured such that a first end is connected to the sensor element 20 and a second end is connected to a separate controller, thereby transmitting a signal detected by the sensor element 20 to the controller. The positioning unit 50 of the present disclosure may be configured to support the contact bush 30 and the disc spring 40 simultaneously, to allow the contact bush 30 to be coupled in the sleeve having a shaft parallel to a longitudinal shaft of the sleeve, i.e., coupled at the center of the sleeve 12. The positioning unit 50 may include a bush lower surface support 51 that supports a lower surface of the contact bush 30 and a bush side surface support 52 that supports a side surface of the contact bush 30.

More specifically, the bush lower surface support 51 may be formed in a shape having an opening at the center thereof, wherein the opening has a diameter that corresponds to a diameter of the lower bush 32 from the center to support the contact bush 30 by being in contact with a lower surface of the upper bush 31. In addition, to be supported by the positioning unit 50, a positioning groove 31-1 may be partially provided at a side surface of the upper bush 31 of the contact bush 30. Preferably, at least two positioning grooves 31-1 may be provided and disposed at symmetrical positions to each other, and may be disposed at predetermined intervals along a circumference of the upper bush 31.

Thus, the bush lower surface support 51 of the positioning unit 50 may support the lower surface of the upper bush 31. However, since the bush lower surface support 51 is not provided at a part of the lower surface on which the positioning groove 31-1 is provided, the bush lower surface support 51 may be formed in a divided shape by being spaced apart from each other. The divided bush lower surface supports 51 may be connected to each other, and the bush side surface support 52 that extends upwardly may be inserted into the positioning groove 31-1.

Therefore, the bush side surface support 52 may be provided in a number that corresponds to a number of the positioning grooves 31-1. For example, according to the exemplary embodiment of the present disclosure, three bush side surface supports 52 may be respectively inserted into three positioning grooves 31-1, and may support the upper bush 31 more stably by maintaining angular distances of about 120 degrees from each other.

Furthermore, the bush lower surface support 51 may include a spring support protrusion 51-1 that protrudes downwardly in an inclined manner. At least two spring support protrusions 51-1 may be provided thereon. Each of the spring support protrusions 51-1 may support a lower surface of the disc spring 40, to allow the disc spring 40 to be coupled with the contact bush 30 while being disposed on the spring support protrusion 51-1. In the exemplary embodiment of the present disclosure, three spring support protrusions 51-1 may be provided, and may support the disc spring 40 more stably by maintaining angular distances of about 120 degrees from each other.

The bush side surface support 52 may be formed in a plate shape having a width that corresponds to a width of the positioning groove 31-1, and the bush side surface support 52 may include a support end bent outward at an upper portion thereof, and thus the support end may be in contact with an inner side surface of the sleeve 12.

Figure 3:
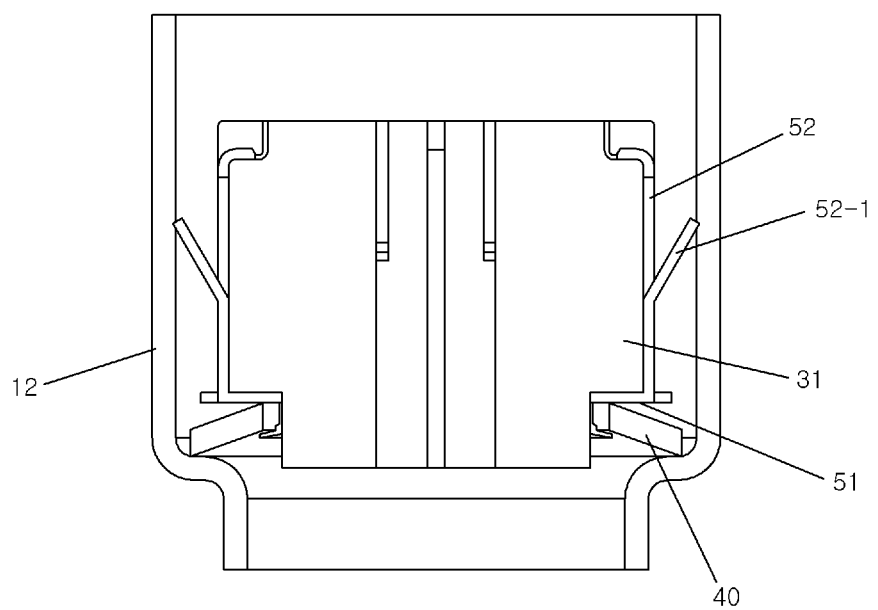
FIG. 3 is a view separately showing a part of FIG. 1.

In addition, as shown in the drawing, the bush side surface support 52 may be divided into three parts in a width direction of the positioning groove 31-1. Both side parts of the divided bush side surface support 52 may be connected to each other at an upper end thereof, and a middle part among the three parts may correspond to the bush side surface support end 52-1 having an upper end bent outward. Accordingly, as shown in FIG. 3, the bush side surface support end 52-1 may be in contact with the inner side surface of the sleeve 12 to support elastically the contact bush 30 to allow the contact bush 30 to be assembled while being positioned at the center of the sleeve 12, and alignment of the contact bush 30 may be maintained even when there is external impact.

Figure 4:
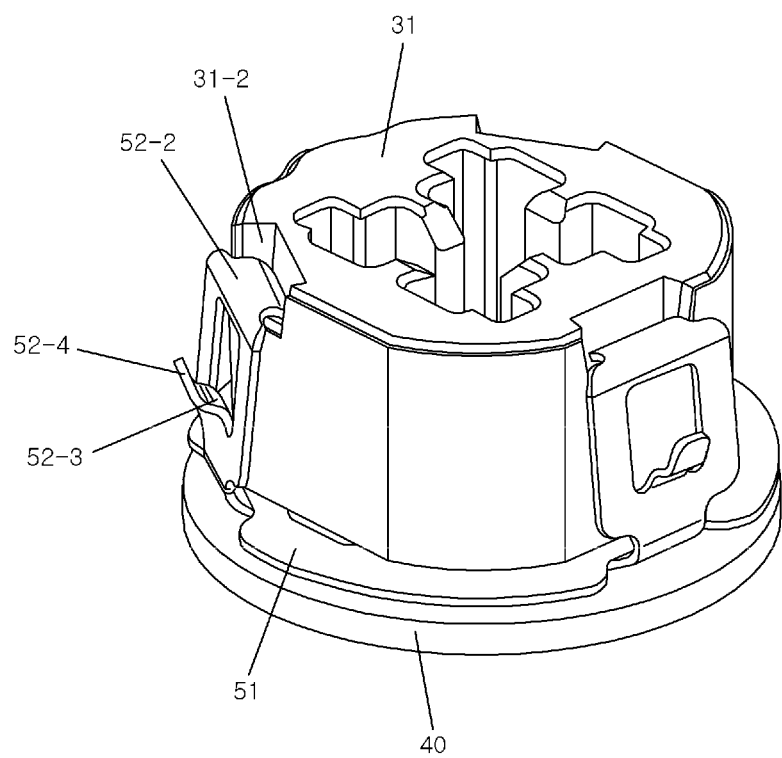
FIG. 4 is a view showing an oxygen sensor for a vehicle according to a second exemplary embodiment of the present disclosure.
Figure 5:
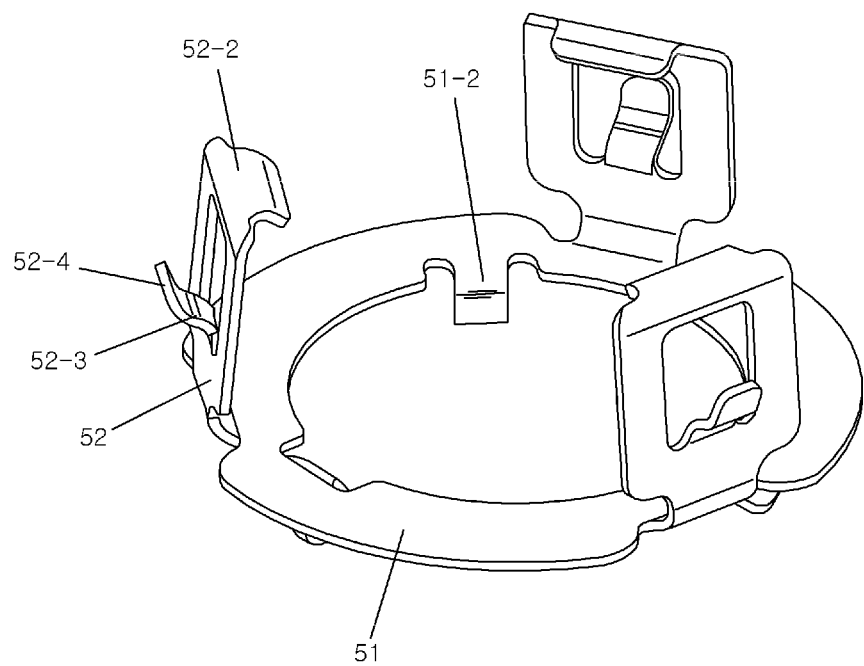
FIG. 5 is a view showing a positioning unit of the oxygen sensor for the vehicle according to the second exemplary embodiment of the present disclosure in FIG. 4.
Figure 6:
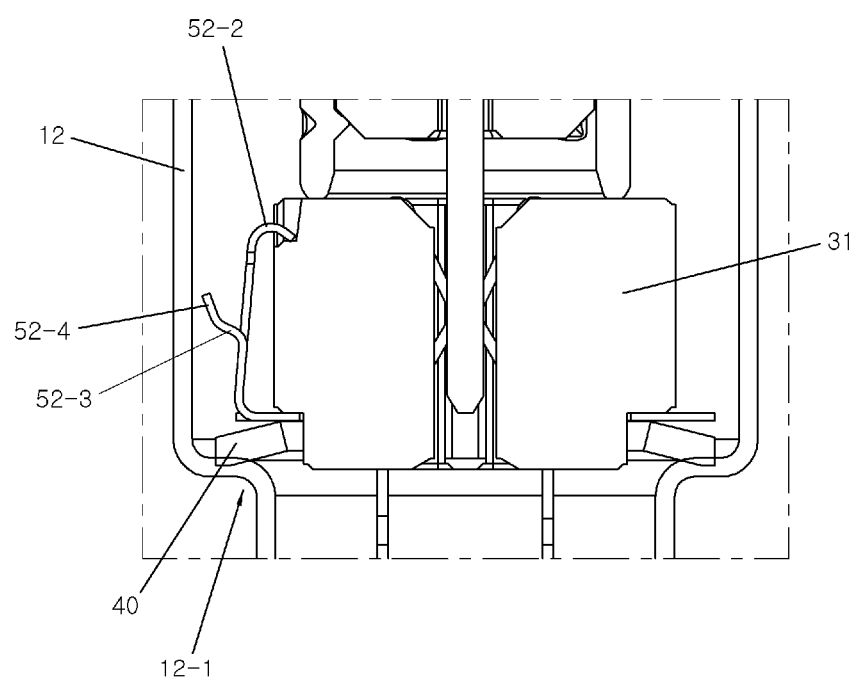
FIG. 6 is a sectional view showing a part of FIG. 4.

Hereinafter, the oxygen sensor for the vehicle according to a second exemplary embodiment of the present disclosure will be described with reference to FIGS. 4 to 6. The description of components that are same as the oxygen sensor for the vehicle according to the first exemplary embodiment described in FIGS. 1 to 3 will be omitted. FIG. 4 is a view showing the oxygen sensor for the vehicle according to the second exemplary embodiment of the present disclosure. FIG. 5 is a view showing a positioning unit of the oxygen sensor for the vehicle according to the second exemplary embodiment of the present disclosure of FIG. 4. FIG. 6 is a sectional view showing a part of FIG. 4.

The oxygen sensor may be formed by coupling the housing 11 having the inner space and the sleeve 12 for coupling with another device. The sensor element 20 may be provided within the inner space formed by the housing 11 and the sleeve 12 to detect oxygen concentration, and the protective tube 13 may be coupled to the housing 11 to protect the sensor element 20 exposed to the upper portion of the housing 11.

The sensor element 20, the contact bush 30, the disc spring 40, and the positioning unit 50 may be provided in the sleeve 12. The sleeve 12 may include the step 12-1 for elastic-support coupling of the contact bush 30 at the middle portion thereof, to allow the lower portion thereof to have the diameter smaller than the diameter of the upper portion thereof with respect to the step 12-1. In addition, the step 12-1 may include a spring seat groove as shown in the drawings, and the outer circumference of the disc spring 40 to be described below may be fitted into the spring seat groove by pressure.

The contact bush 30 may be coupled in the sleeve while being elastically supported by the disc spring 40 that is disposed on the step 12-1 and fitted into the spring seat groove by pressure (e.g., by a press fit or an interference fit). In addition, the disc spring 40 may be formed in the plate shape with the central aperture and may have the shape of being inclined downwardly in the sectional view. Accordingly, the outer circumference of the disc spring 40 may be disposed on the step 12-1, and the inner circumference thereof may support the step of the contact bush 30.

The contact bush 30 may include the upper bush 31 and the lower bush 32, the upper bush 31 being open upwardly to form the sensor groove into which the sensor element 20 is inserted and the lower bush 32 being open downwardly to form the terminal groove 32-1 into which the contact terminal T is inserted. The lower bush 32 may have the diameter smaller than the diameter of the upper bush 31, to allow the step to be formed between the upper bush 31 and the lower bush 32.

In addition, the contact terminal T may be configured such that the first end is connected to the sensor element 20 and the second end is connected to the separate controller, thereby transmitting the signal detected by the sensor element 20 to the controller. Thus, the positioning unit 50 of the second exemplary embodiment may support the contact bush 30 and the disc spring 40 simultaneously, to allow the contact bush 30 to be coupled in the sleeve having the shaft parallel to the longitudinal shaft of the sleeve 12, i.e., coupled at the center of the sleeve 12.

The positioning unit 50 may include the bush lower surface support 51 that supports the lower surface of the contact bush 30 and the bush side surface support 52 that supports the side surface of the contact bush 30. More specifically, the bush lower surface support 51 may be formed in the shape having the opening at the center thereof, wherein the opening has the diameter that corresponds to the diameter of the lower bush 32 from the center to support the contact bush 30 by being in contact with the lower surface of the upper bush 31.

In addition, to be supported by the positioning unit 50, a positioning groove 31-2 may be partially provided at the side surface of the upper bush 31 of the contact bush 30. Preferably, at least two positioning grooves 31-2 may be provided and disposed at symmetrical positions to each other, and may be disposed at predetermined intervals along the circumference of the upper bush 31. Specifically, in the second exemplary embodiment, the positioning grooves 31-2 may be partially formed on the upper portion of the side surface of the upper bush 31, thereby allowing a support end 52-2 of the bush side surface support 52 described below to be disposed thereon and supported.

Accordingly, the bush lower surface support 51 of the positioning unit 50 may support the lower surface of the upper bush 31, but may not be provided at the part of the lower surface at which the positioning groove 31-2 is provided. Thus, the bush lower surface supports 51 may be formed in the divided shape by being spaced apart from each other. The divided bush lower surface supports 51 may be connected to each other, and the bush side surface support 52 that extends upwardly may include the support end 52-2 having the upper end bent toward the center of the contact bush 30, to allow the support end 52-2 to be inserted into the positioning groove 31-2 for support. Therefore, the number of bush side surface support 52 may correspond to the number of the positioning grooves 31-2. For example, in the exemplary embodiment, three support ends 52-2 may be respectively inserted into three positioning grooves 31-2, and may support the upper bush 31 more stably by maintaining angular distances of about 120 degrees from each other.

Furthermore, the bush lower surface support 51 may include a spring support protrusion 51-2 that protrudes downwardly in a curved manner. At least two spring support protrusions 51-2 may be provided thereon. Each of the spring support protrusions 51-2 may support the lower surface of the disc spring 40 to allow the disc spring 40 to be coupled with the contact bush 30 while being disposed on the spring support protrusion 51-2. In the exemplary embodiment, three spring support protrusions 51-2 may be provided, and may support the disc spring 40 more stably by maintaining angular distances of about 120 degrees from each other. For easy and stable placement and support of the disc spring 40, the spring support protrusion 51-2 may extend downwardly from the inside of the bush lower surface support 51, and then curve outward from the bush lower surface support 51.

The bush side surface support 52 may include the bush side surface support end that protrudes outward, and the bush side surface support end may be in contact with the inner side surface of the sleeve 12. In addition, as shown in the drawing, the bush side surface support 52 may be formed in the shape of being divided into three parts in the width direction of the positioning groove 31-2. Both side portions of the divided bush side surface support 52 may be connected to each other at an upper end thereof, and the middle part among the three parts may be configured as the bush side surface support end having an upper end thereof bent outward. In the exemplary embodiment, the bush side surface support end may have a double-bent shape unlike the shape of the support end of the first exemplary embodiment, and may extend by protruding outward from the bush side surface support 52.

In other words, the bush side surface support end may include a first curved portion 52-3 bent outwardly from a lower portion thereof and a second curved portion 52-4 bent in the opposite direction from the first curved portion 52-3, i.e., curved inwardly. Accordingly, the bush side surface support end may reduce friction when the bush side surface support end is in contact with the inner side surface of the sleeve 12, and may realize a buffering (e.g., shock absorbing) function by an elastic force. Thus, the bush side surface support end 52-3 and 52-4 may be in contact with the inner side surface of the sleeve 12 to elastically support the contact bush 30, to allow the contact bush 30 to be assembled at the center of the sleeve 12 and the alignment of the contact bush 30 to be maintained even when there is external impact.

As described above, the oxygen sensor for the vehicle of the present disclosure may allow the contact bush to be coupled with the sensor element and the contact terminal to be in a particular position, and may be improved in stability against the external impact to further improve durability of components.

Although the present disclosure was described with reference to the accompanying drawings, it should be understood that the present disclosure is not limited to the exemplary embodiments disclosed in the description, and may be changed and modified in various ways by those skilled in the art without departing from the spirit and scope of the present disclosure described in the appended claims. Accordingly, it should be understood that the modifications and the additions are included in the claims of the present disclosure, and the rights of the present disclosure may be interpreted on the basis of the accompanying claims.

What is claimed is:

1. An oxygen sensor for a vehicle, the oxygen sensor comprising: a housing; a sleeve coupled to a side of the housing; a sensor element configured to determine an oxygen concentration and provided within an inner space defined by the housing and the sleeve; a contact terminal connected to the sensor element; a contact bush including an upper bush and a lower bush, the upper bush being open upwardly to form a sensor groove into which the sensor element is inserted and the lower bush being open downwardly to form a terminal groove into which the contact terminal is inserted; and a positioning unit coupled with the contact bush, wherein the positioning unit maintains a gap between a circumference of the contact bush and an inner side surface of the sleeve, wherein the upper bush includes at least two positioning grooves at a side surface thereof, the positioning unit includes at least two bush side surface supports inserted into the at least two positioning grooves, and each of the bush side surface supports includes a bush side surface support end that is bent outward to allow the bush side surface support end to be in contact with the inner side surface of the sleeve.

2. The oxygen sensor of claim 1, wherein the bush side surface support is divided into three parts in a width direction of the positioning groove, and the bush side surface support end that is bent outward corresponds to an upper end of a middle part among the three parts of the bush side surface support.

3. The oxygen sensor of claim 1, further comprising:
a disc spring formed in a plate shape with a central aperture, the disc spring being inclined downwardly in a sectional view, wherein an outer circumference of the disc spring is disposed on the sleeve, and an inner circumference of the disc spring supports the contact bush,
wherein the positioning unit comprises:
a bush lower surface support that supports a lower surface of the contact bush, the bush lower surface support including at least two spring support protrusions which protrude downwardly with an inclination to support a lower surface of the disc spring.

4. The oxygen sensor of claim 3, wherein the sleeve includes a step at a center part thereof, to allow a diameter of a lower part of the sleeve to be smaller than a diameter of an upper part thereof with respect to the step, and the outer circumference of the disc spring is fitted into a spring seat groove provided on the step of the sleeve by pressure.

5. The oxygen sensor of claim 3, wherein the lower bush of the contact bush has a smaller diameter than the upper bush to allow a step to be formed between the lower bush and the upper bush, and the inner circumference of the disc spring supports the step between the upper bush and the lower bush.

6. The oxygen sensor of claim 5, wherein the sleeve includes a step at a center part thereof to allow a diameter of a lower part of the sleeve to be smaller than a diameter of an upper part thereof with respect to the step, and the outer circumference of the disc spring is disposed on the step of the sleeve.

7. An oxygen sensor for a vehicle, the oxygen sensor comprising: a housing; a sleeve coupled to a side of the housing; a sensor element configured to determine an oxygen concentration and provided within an inner space defined by the housing and the sleeve; a contact terminal connected to the sensor element; a contact bush including an upper bush and a lower bush, the upper bush being open upwardly to form a sensor groove into which the sensor element is inserted and the lower bush being open downwardly to form a terminal groove into which the contact terminal is inserted; and a positioning unit coupled with the contact bush, wherein the positioning unit maintains a gap between a circumference of the contact bush and an inner side surface of the sleeve, wherein the positioning unit comprises:

a bush lower surface support that supports a lower surface of the contact bush; and
a bush side surface support that supports a side surface of the contact bush,
wherein the upper bush includes at least two positioning grooves partially formed on an upper portion of a side surface of the upper bush, and the bush side surface support includes a support end at a position that corresponds to each of the at least two positioning grooves, the support end is bent from an upper end thereof and is inserted into the positioning groove, and
wherein the bush side surface support includes a bush side surface support end that protrudes outward, and the bush side surface support end is in contact with the inner side surface of the sleeve.

8. The oxygen sensor of claim 7, further comprising:
a disc spring formed in a plate shape with a central aperture, the disc spring being inclined downwardly in a sectional view, wherein an outer circumference of the disc spring is disposed on the sleeve, and an inner circumference of the disc spring supports the contact bush.

9. The oxygen sensor of claim 7, wherein the bush side surface support end includes a first curved portion and a second curved portion, the first curved portion being bent outward from a lower portion thereof and the second curved portion being bent inward from the first curved portion.

10. The oxygen sensor of claim 9, wherein the bush lower surface support includes at least two spring support protrusions which extend downwardly from an inside of the bush lower surface support and then are curved outwardly from the bush lower surface support.

* * * * *